United States Patent
Lee

(10) Patent No.: US 7,104,767 B2
(45) Date of Patent: Sep. 12, 2006

(54) DIAPHRAGM PUMP FOR MEDICAL APPLICATIONS

(75) Inventor: J. Kelly Lee, Rochester, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 0 days.

(21) Appl. No.: 11/025,414

(22) Filed: Dec. 29, 2004

(65) Prior Publication Data

US 2006/0013710 A1    Jan. 19, 2006

Related U.S. Application Data

(60) Provisional application No. 60/588,668, filed on Jul. 19, 2004.

(51) Int. Cl.
*F04B 17/03* (2006.01)
(52) U.S. Cl. .................................. 417/413.1
(58) Field of Classification Search ............. 417/413.1, 417/50
See application file for complete search history.

(56) References Cited

U.S. PATENT DOCUMENTS

| | | | |
|---|---|---|---|
| 2,312,712 A * | 3/1943 | Hartline | 417/413.1 |
| 2,787,444 A * | 4/1957 | Skarstrom | 417/413.1 |
| 2,930,324 A * | 3/1960 | Toulmin, Jr. | 417/413.1 |
| 3,379,191 A | 4/1968 | Harvey | |
| 3,381,623 A * | 5/1968 | Elliott | 417/413.1 |
| 3,706,893 A | 12/1972 | Olsen et al. | |
| 3,884,718 A | 5/1975 | Deaton et al. | |
| 4,786,240 A * | 11/1988 | Koroly et al. | 417/413.1 |
| 4,822,357 A | 4/1989 | Forster et al. | |
| 4,824,336 A * | 4/1989 | Iwaki et al. | 417/413.1 |
| 4,838,887 A | 6/1989 | Idriss | |
| 4,944,659 A | 7/1990 | Labbe et al. | |
| 5,011,380 A * | 4/1991 | Kovacs | 417/413.1 |
| 5,045,064 A | 9/1991 | Idriss | |
| 5,049,141 A | 9/1991 | Olive | |
| 5,382,236 A | 1/1995 | Otto et al. | |
| 5,599,174 A * | 2/1997 | Cook et al. | 417/413.1 |
| 6,185,452 B1 | 2/2001 | Schulman et al. | |
| 6,232,680 B1 * | 5/2001 | Bae et al. | 417/413.1 |
| 6,238,812 B1 | 5/2001 | Brown et al. | |
| 6,479,920 B1 | 11/2002 | Lal et al. | |
| 6,514,047 B1 | 2/2003 | Burr et al. | |
| 6,537,268 B1 | 3/2003 | Gibson et al. | |
| 6,589,229 B1 | 7/2003 | Connelly et al. | |

(Continued)

FOREIGN PATENT DOCUMENTS

JP        401170777 A *   7/1989

*Primary Examiner*—Michael Koczo, Jr.
(74) *Attorney, Agent, or Firm*—Eleanor M. Hynes; Hiscock & Barclay, LLP

(57) ABSTRACT

An implantable diaphragm pump for use in medical applications comprising a housing having a pump cap, a valve plate, a diaphragm, and a base plate, wherein the pump cap and the valve plate are separated by the diaphragm, and the valve plate and lower surface of the diaphragm serve to form a pump chamber. A permanent magnet is attached to the pump cap within the diaphragm chamber wherein the lower surface of the permanent magnet is adjacent to the upper surface of the diaphragm. The diaphragm having a coil and a corrugated outer periphery, wherein when electrical current flows in a first direction through the coil, the diaphragm engages the lower surface of the permanent magnet, and when electrical current flows in a direction opposite the first direction, said diaphragm engages the upper surface of the valve plate.

11 Claims, 3 Drawing Sheets

U.S. PATENT DOCUMENTS 6,843,643 B1 * 1/2005 Fukami et al. ........... 417/413.1
2002/0087147 A1 7/2002 Hooper et al.
2002/0173773 A1 11/2002 Olsen
2003/0006668 A1 1/2003 Lal et al.
2003/0085684 A1 5/2003 Tsukamoto et al.
2003/0135160 A1 7/2003 Grey et al.
2004/0059392 A1 3/2004 Parramon et al.

* cited by examiner

DIAPHRAGM PUMP FOR MEDICAL APPLICATIONS

CROSS-REFERENCE TO RELATED APPLICATION

The present application claims priority based on provisional application Ser. No. 60/588,668, filed Jul. 19, 2004.

FIELD OF THE INVENTION

The present invention relates to a pump for medical applications, more particularly, to miniature or micro-pumps used in medical applications for delivering small quantities of therapeutic drugs.

BACKGROUND OF THE INVENTION

Miniature or micro-pumps are currently used for a variety of medical purposes. Such devices are implantable in the human body and serve to deliver small quantities of therapeutic drugs. Currently, implantable infusion pumps are known to utilize a solenoid to drive a small piston. Because it is essential for these pumps to be both precise and reliable, the stroke length and cylinder bore must be precisely made, thereby allowing the pump to deliver a well controlled volume of fluid with each stroke. Manufacturing and assembly of miniature precision equipment of this type is extremely expensive requiring specialized tooling and inspection techniques.

Furthermore, because these pumps are to be used as part of an implantable drug system, it is desirable that they be relatively thin so that they may be easily integrated into these systems. Additionally, the cylindrical shape of a piston pump, is cumbersome for such applications, and tends to take up more space than a relatively flat object such as a diaphragm pump would. While many of the prior art pumps contain diaphragms, the systems generally work in conjunction with a piston or solenoid.

For example, turning now to the prior art patents, U.S. Pat. No. 6,537,268 to Gibson et al. discloses an infusion pump having a compressible source of compliance, such as, a plurality of diaphragms serving as pillows. While the prior art utilizes a pumping mechanism, it specifically requires a piston pump to compress the aforementioned diaphragms.

Also, U.S. Patent Application Publication 2003/0135160 to Gray et al. discloses a drive mechanism for an infusion device having a coil surrounding a piston channel, the piston is located within the piston channel. In the retracted position the a piston chamber is formed between the piston and valve member, and filled with a fluid. When the piston is moved into the forward position chamber volume is reduced and pressure increases, moving the valve member to the open position to thereby discharge the fluid.

Finally, U.S. Patent Application Publication 2002/0173773 to Olsen discloses an implantable substance delivery device having a permanent magnet solenoid pump. The pump piston is moveable within the pump cylinder wherein a fluid contained in the inlet chamber is displaced when the pump piston retracts. The fluid contained within the pumping chamber is displaced when the pump piston is actuated.

Therefore, what is needed in the art is an implantable pump that eliminates the need for components having tight tolerances such as those found in miniature piston pumps.

Furthermore, what is needed in the art is an implantable pump that is relatively thin and may be integrated easily into medical devices worn just beneath the skin.

SUMMARY OF THE INVENTION

It is therefore, a primary object of this invention to provide a new and improved micro-pump for use in medical applications such as delivering small quantities of therapeutic drugs.

An advantage of the present invention is that it eliminates the need for components having tight tolerances such as those found in miniature piston pumps.

Another advantage of the present invention is that the diaphragm pump is relatively disk-shaped and may be integrated easily into medical devices worn just beneath the skin.

The present invention provides an implantable diaphragm pump for use in medical applications comprising a housing having a pump cap, a valve plate having a textured surface, a diaphragm, and a base plate, wherein the valve plate and lower surface of the diaphragm serve to form a pump chamber. A permanent magnet is attached to the pump cap wherein the lower surface of the permanent magnet is adjacent to the upper surface to the diaphragm. The diaphragm has a corrugated outer periphery and a coil attached thereto. An electrical current applied to the coil in a first direction causes the diaphragm to engage the lower surface of the permanent magnet. An electrical current applied to the coil in the opposite direction to the first direction, causes the diaphragm to move away from the permanent magnet and engage the upper surface of the valve plate.

An additional embodiment of the present invention provides an implantable diaphragm pump for use in medical applications comprising a valve plate, a base plate, and a diaphragm. The upper surface of the diaphragm having a piezoelectric material attached thereto, and the lower surface of the diaphragm and the valve plate serve to form a pump chamber. A means for supplying a voltage to the piezoelectric material is included, wherein the application of the voltage to the piezoelectric element shall cause the lower surface of the diaphragm to move toward or away from the upper surface of the valve plate.

BRIEF DESCRIPTION OF THE DRAWINGS

The above-mentioned and other features and advantages of this invention, and the manner of attaining them, will become apparent and be better understood by reference to the following description of several embodiments of the invention in conjunction with the accompanying drawings, wherein:

FIG. 2 is a plan view of the valve plate of FIG. 1a;

FIG. 3 is a map of the magnetic flux pattern over the cross-sectional view of the diaphragm pump of FIG. 1a.

Corresponding reference characters indicate corresponding parts throughout the several views. The examples set out herein illustrate several embodiments of the invention but should not be construed as limiting the scope of the invention in any manner.

DESCRIPTION OF THE PREFERRED EMBODIMENTS

Figure 1A:
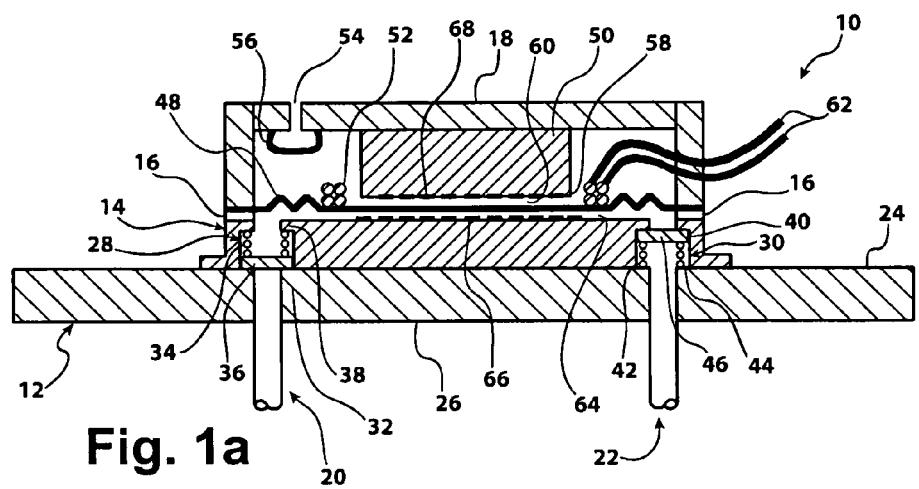
FIG. 1a is a cross-sectional view of a diaphragm pump according to a first embodiment of the invention.
Figure 1B:
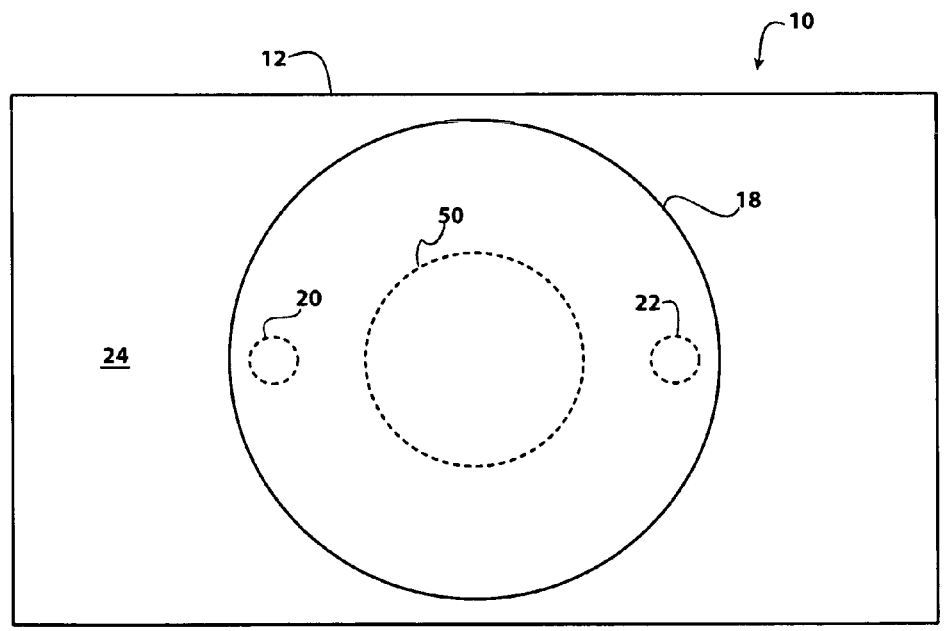
FIG. 1b is a plan view of the diaphragm pump of FIG. 1a with the permanent magnet and inlet and outlet bores shown in phantom.

Referring now to the drawings, FIGS. 1a and 1b illustrate the micro-diaphragm pump 10 of the present invention. The body of the device of the present invention comprises a base plate 12, a valve plate 14, a spacer ring 16, and a cap 18. The base plate 12 comprises a pair of cylindrical bores, more particularly an inlet bore 20 and an outlet bore 22. Generally, a capillary or tube may be inserted within the aforementioned bores 20 and 22 for delivering and dispensing a fluid as necessary. The addition of the aforementioned tubes serves to assure that the fluids do not come in contact with the material of the base plate 12. Wherever possible, the component parts of the pump that come in contact with the fluid or the human body itself are made from a titanium alloy known to be inert to fluids used in medical applications and inert to body chemistry. The base plate 12 is constructed of a soft magnetic material such as 29-4 stainless steel which is highly corrosion resistant but also good as a soft magnetic material. Additionally, the base plate 12 further comprises an upper surface 24 and a lower surface 26, wherein the base plate upper surface 24 is adjacent to the lower surface of the valve plate 14.

The valve plate 14 comprises an inlet valve 28 and an outlet valve 30, which are adjacent to the inlet bore 20 and the outlet bore 22 of the base plate 12, respectively. The inlet valve 28 comprises an inlet valve seat 32, an inlet biasing means 34, and an inlet valve cover 36. The inlet valve seat 32 is formed by the portion of the base plate upper surface 24 proximate to the inlet bore 20. The inlet biasing means 34 abuts against an inlet rim 38 formed in the valve plate 14 and biases the inlet valve cover 36 against the inlet valve seat 32. The outlet valve 30 comprises an outlet valve seat 40, an outlet biasing means 42, and an outlet valve cover 44. The outlet valve seat 40 is formed by an outlet rim 46 formed in the valve plate 14. The outlet biasing means 42 abuts against the base plate upper surface 24 proximate to the outlet bore 22 and biases the outlet valve cover 44 against the outlet valve seat 40.

The spacer ring 16 and a primary diaphragm 48 are above the upper surface of the valve plate 14, thereby serving to form a chamber for receiving and dispensing the fluid. The spacer ring 16 may vary in thickness, but it is desirable for the thickness to be adequate to allow the actuator to travel a sufficient distance to maintain a compression ratio at or above 3:1. This minimum ratio is required to assure that trapped air bubbles do not shut down the pump. The primary diaphragm 48 comprises a corrugated outer periphery, allowing the diaphragm to travel toward or away from the valve plate 14. The stroke of the primary diaphragm 48 and the resulting volume of fluid delivered by the pump 10 is therefore defined by the thickness of the spacer ring 16. Varying the thickness of the spacer ring 16 allows the pump delivery volume to be controlled in manufacturing. The delivered volume per stroke may also be altered, thus addressing use of the pump 10 in a greater variety of applications.

Adjacent to the upper surface of the primary diaphragm 48, the cap 18 houses a permanent magnet 50. In operation, the permanent magnet 50 operates in conjunction with a coil 52 attached to the upper surface of the primary diaphragm 48, in a similar manner to a speaker, thereby serving as the actuation means for the pump 10. Additionally, since the pump 10 is designed to operate near atmospheric pressure, a breather hole 54 and an equalization diaphragm 56 are provided in the cap 18, thereby serving to equalize the pressure between the environment and the chamber formed by the cap 18 and the primary diaphragm 48. The equalization diaphragm 56 around the breather hole 54 maintains the clean environment around the permanent magnet 50 and coil 52, thus eliminating the need for corrosion protection of the magnet.

As stated above, the device of the present invention operates on a similar principal as an audio speaker. As illustrated in FIG. 1a, a coil 52 is fixedly attached to the upper surface of the primary diaphragm 48. Because it is desirable for the pump 10 to be as flat as possible, the coil 52 is mounted proximate to the tip 58 of the permanent magnet 50, but not in the gap 60. The permanent magnet 50 may be constructed from any suitable material, such as neodymium-iron-boron or samarium-cobalt, having high coercivity and high residual induction. Additionally, a pair of coil leads 62 provide a means for energizing the coil 52. While FIG. 1a shows a pair of coil leads 62 penetrating the sidewall of the cap 18, any suitable method of attaching the coil leads 62 to the coil 52 is considered to be within the scope of the invention.

In operation, when the electrical current flowing through the coil 52 changes direction, the polar orientation of the coil 52 reverses. This changes the magnetic forces between the coil 52 and the permanent magnet 50, thereby moving the coil 52 and attached primary diaphragm 48 toward or away from the valve plate 14. As the primary diaphragm 48 moves away from the valve plate 14, it serves to open the inlet valve 28, thereby drawing the fluid through the inlet 20, into the area between the primary diaphragm 48 and valve plate 14, hereinafter referred to as the pump chamber 64. As the primary diaphragm 48 approaches the valve plate 14, the fluid in the pump chamber 64 serves to direct a force on the outlet valve cover 44 sufficient to counter the outlet biasing means 42, thereby dispensing the fluid stored in the pump chamber 64.

The primary diaphragm 48 is made from titanium alloy such at Ti Grade 1–4 or Grade 5 which is desirable for medical applications and does not react with body chemistry or fluids typically used in medical applications. Additionally, the valve plate 14 is made from titanium such as Ti Grade 1—4 or Grade 5. The inlet valve cover 36 and the outlet valve cover 44 are made from silicone rubber. The base plate 12, which does not come in contact with the fluid, is made from a soft magnetic material such as 29-4 stainless steel which is highly corrosion resistant but also good as a soft magnetic material. As stated above, wherever possible, the component parts of the pump 10 that come in contact with the fluid or the human body should be constructed from a titanium alloy known to be inert to fluids used in medical applications and inert to body chemistry.

Furthermore, the aforementioned soft magnetic material of the base plate 12 has been selected so that it may serve to shield the permanent magnet 50 from large external fields, such as those experienced, during magnetic resonance imaging (MRI). Furthermore, as illustrated in FIG. 1a, the pump 10 has been designed so that the base plate 12 is an appreciable distance from the face of the permanent magnet 50. Large external fields would otherwise serve to partially de-pole the permanent magnet 50.

Figure 2:
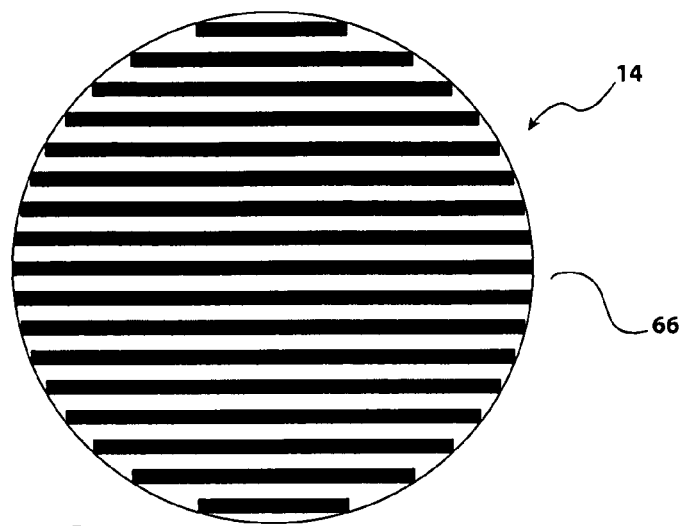

As stated above, the outer periphery of the primary diaphragm 48 has a corrugated section so as to permit the primary diaphragm 48 to move up and down. As the primary diaphragm 48 moves toward or away from the valve plate 14, it alternatively comes in contact with the valve plate 14 and the permanent magnet 50. Referring now to FIG. 2, a first raised pattern 66 is machined on the valve plate 14 at the center of the pump 10. Additionally, a similar second raised pattern 68 is machined on the surface of the magnet 50, proximate to the primary diaphragm 48. The purpose of the raised patterns 66 and 68 is to prevent the primary diaphragm 48 from adhering to the valve plate 14 or the permanent magnet 50. The raised patterns 66 and 68 are generally disposed as grooves running in the direction of the fluid flow. This orientation allows any bubbles in the fluid to move through the pump 10 in the direction of flow to thereby minimize the trapping of bubbles, a known cause of pump failure. Additionally, as stated earlier, trapped air bubbles can shut down the pump unless a compression ratio of the pump is at least 3:1 is maintained and the spacer ring 16 must be thick enough that the actuator travel is sufficient to maintain the compression ratio at or above this level. The compression ratio in this case shall be defined as the ratio between the volume of the pump chamber 64 when the primary diaphragm 48 is fully pressed against the magnet 50 to the volume of the chamber 64 when the primary diaphragm 48 is biased to press against the valve plate 14 when current does not flow through the coil 52.

Figure 3:
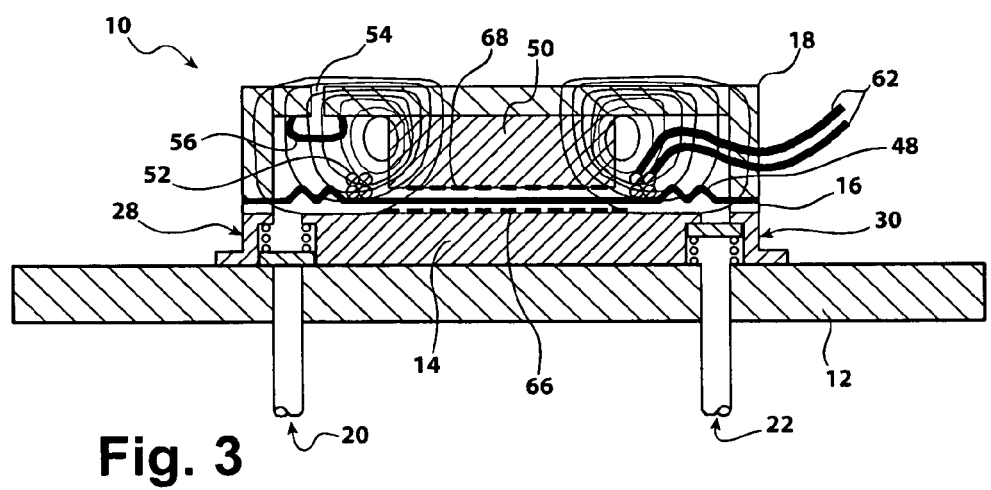

Referring now to FIG. 3, the magnetic flux pattern surrounding the permanent magnet 50 is shown. Generally for high energy magnets such as samarium cobalt and neodymium-iron-boron, magnetic flux lines are particularly strong around the tip of the magnet. The magnetically soft cap 18 used for audio speaker motors is typically placed close to the magnet 50 in order to concentrate the flux. Additionally, while a thin and long coil 50 is utilized for a particular embodiment of the present invention, any suitable coil is considered to be within the scope of the invention. Additionally, an embodiment is contemplated wherein the entire primary diaphragm 48 is enclosed on the inside of cap to take advantage of the strong field near the tip of the magnet 50. The coil leads 62 may be constructed from Litz wire, or flat spiral springs made from a material such as phosphor-bronze.

Figure 4:
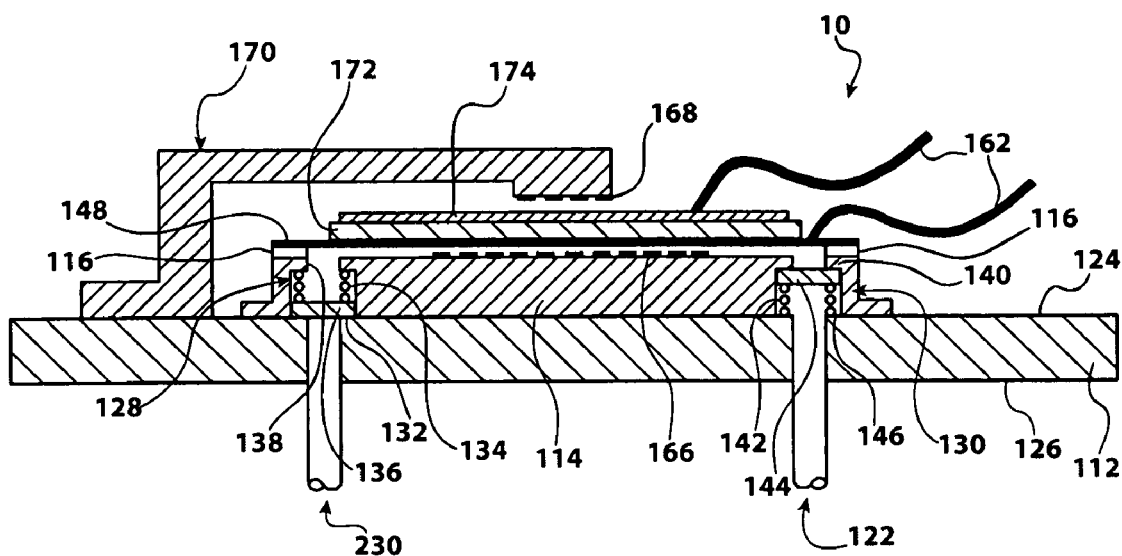
FIG. 4 is a cross-sectional view of a diaphragm pump according to a second embodiment of the invention.

Referring now to FIG. 4, an alternative embodiment of the present invention is shown. The micro-diaphragm pump 110 of this particular embodiment comprises a base plate 112, a valve plate 114, a spacer ring 116, and a return stop arm 170. The base plate 112 comprises a pair of cylindrical bores, more particularly an inlet bore 120 and an outlet bore 122. Generally, a capillary or tube may be inserted in the aforementioned bores 120 and 122 for delivering and dispensing a fluid as necessary. The addition of the aforementioned tubes serves to assure that the fluids do not come in contact with the material of the base plate 112. Wherever possible, the component parts of the pump 110 that come in contact with the fluid or the human body itself are made from a titanium alloy known to be inert to fluids used in medical applications and inert to body chemistry. The base plate 112 is constructed of a soft magnetic material such as 29-4 stainless steel which is highly corrosion resistant but also good as a soft magnetic material. The base plate 112 further comprises an base plate upper surface 124 and a base plate lower surface 126, wherein said base plate upper surface 124 is adjacent to the lower surface of the valve plate 114.

The valve plate 114 comprises an inlet valve 128 and an outlet valve 130, which are respectively adjacent to the inlet bore 120 and the outlet bore 122 of the base plate 112. The inlet valve 128 comprises an inlet valve seat 132, an inlet biasing means 134, and an inlet valve cover 136. The inlet valve seat 132 is formed by the portion of the base plate upper surface 124 proximate to the inlet bore 120. The inlet biasing means 134 abuts against an inlet rim 138 formed in the valve plate 114 and biases the inlet valve cover 136 against the inlet valve seat 132. The outlet valve 130 comprises an outlet valve seat 140, an outlet biasing means 142, and an outlet valve cover 144. The outlet valve seat 140 is formed by an outlet rim 146 formed in the valve plate 114. The outlet biasing means 142 abuts against the base plate upper surface 124 proximate to the outlet bore 122 and biases the outlet valve cover 144 against the outlet valve seat 140.

The conductive spacer ring 116 and a diaphragm 148 are located above the valve plate 114, thereby serving to form a pump chamber 164 for receiving and dispensing a fluid. Varying the thickness of the spacer ring 116 allows the pump delivery volume to be controlled in manufacturing. The delivered volume per stroke may also be altered, thus addressing use of the pump 110 in a greater variety of applications.

In the embodiment illustrated in FIG. 4, a piezoelectric actuator 172 is used as the motive force to deform the titanium membrane. The piezoelectric actuator 172 has a high d31 constant and is optimized in thickness to provide the maximum deformation of the diaphragm 148. While this particular embodiment uses lead-zirconate-titanate piezoelectric materials such as PZT-5B or PZT-5H, other piezoelectric materials may be used and are considered within the scope of the invention.

The aforementioned piezoelectric actuator 172 is between an electrode 174 and the diaphragm 148. In the illustrated embodiment the electrode 174 is screen printed and fired onto the piezoelectric actuator 172. Furthermore, the diaphragm 148 serves as the second electrode. The diaphragm 148 is grounded through the conductive ring spacer 116 to the valve plate 114 and base plate 112. A pair of electrical leads 162 are made of a material such as Litz wire or spiral springs. One of the electric leads 162 is bonded to the electrode 174 and the other is bonded to the diaphragm 148. The diaphragm 148 bottoms on the valve plate 114 and the return stop arm 170 limits the travel in the upward or return stroke direction. Both the valve plate 114 and the stop arm 170 are textured in such a way as to reduce the surface contact area with respective patterns 166 and 168. The patterns 166 and 168 are similar to the pattern 66 shown in FIG. 2.

Alternatively, the piezoelectric actuator 172 is isolated from the base plate 112 simply by replacing the conductive ring spacer 116 with a non-conductive spacer ring. In this instance, the patterns 166 and 168 are made of a material that is non-conductive, such as a screen printed epoxy compatible with the fluids involved.

Furthermore, the piezoelectric actuator 172 may be driven bi-directionally against both the upper and the lower stops to reduce the effect of piezoelectric creep.

The adjustable spacer ring allows simplified manufacture of an accurate pump because tight manufacturing tolerances of the pump components are not needed. Further, the fact that the travel of the diaphragm is controlled by the distance between the valve plate and the magnet in the first embodiment and the return stop arm in the second embodiment means that control of the pump is simplified. This is because the compression ratio is fixed by the spacer ring and is not controlled by the magnitude of the electric current supplied to the pump. The affect the magnitude of the electric current has on the travel of the diaphragm may change over time or be influenced by outside electromagnetic fields.

While this invention has been described as having a preferred design, the present invention can be further modified within the spirit and scope of this disclosure. This application is therefore intended to cover any variations, uses, or adaptations of the present invention using the general principles disclosed herein. Further, this application is intended to cover such departures from the present disclosure as come within the known or customary practice in the art to which this invention pertains and which fall within the limits of the appended claims.

What is claimed is:

1. An implantable micro-diaphragm pump for use in medical applications comprising:
   a housing comprising a valve plate and a micro-diaphragm;
   a pump chamber between said valve plate and said micro-diaphragm;
   a permanent magnet being proximate to said micro-diaphragm;
   said micro-diaphragm comprising a coil, wherein varying the direction of electrical current applied to said coil shall cause the micro-diaphragm to engage either the permanent magnet or the valve plate.

2. The micro-diaphragm pump of claim 1, wherein said housing further comprises a pump cap that supports said permanent magnet and a base plate that supports said valve plate.

3. The implantable micro-diaphragm pump of claim 2, wherein said pump cap and said valve plate are separated by said micro-diaphragm.

4. The micro-diaphragm pump of claim 1, wherein said micro-diaphragm further comprises a corrugated outer periphery.

5. The implantable micro-diaphragm pump of claim 1 further comprising a spacer ring between said micro-diaphragm and said valve plate, wherein varying the thickness of said spacer ring shall vary the volume of the pump chamber.

6. The implantable micro-diaphragm pump of claim 1 further comprising an inlet and an outlet wherein the pump shall serve to either draw fluid into said pump chamber through said inlet or deliver a metered dose of said fluid through said outlet dependant upon the polarity of the coil.

7. An implantable diaphragm pump for use in medical applications comprising:
   a. a housing comprising a valve plate, a diaphragm, a pump cap, and a base plate that supports said valve plate;
   b. a pump chamber between said valve plate and said diaphragm;
   c. a permanent magnet being proximate to said diaphragm;
   d. said diaphragm comprising a coil, wherein varying the direction of electrical current applied to said coil shall cause the diaphragm to engage either the permanent magnet or the valve plate;
   e. said pump cap and said diaphragm form a chamber; and
   f. said pump cap further comprises a breather hole to equalize pressure between the chamber and the environment.

8. The implantable micro-diaphragm pump of claim 7 further comprising a membrane between said breather hole and said chamber.

9. An implantable diaphragm pump for use in medical applications comprising:
   a housing comprising a valve plate and a diaphragm;
   a pump chamber between said valve plate and said diaphragm;
   a permanent magnet being proximate to said diaphragm, wherein said permanent magnet comprises a textured surface to thereby impede said diaphragm from sticking to said permanent magnet; and
   said diaphragm comprising a coil, wherein varying the direction of electrical current applied to said coil shall cause the diaphragm to engage either the permanent magnet or the valve plate.

10. An implantable diaphragm pump for use in medical applications comprising:
    a housing comprising a valve plate and a diaphragm, wherein said valve plate comprises a textured surface to thereby impede said diaphragm from sticking to said valve plate;
    a pump chamber between said valve plate and said diaphragm;
    a permanent magnet being proximate to said diaphragm; and
    said diaphragm comprising a coil, wherein varying the direction of electrical current applied to said coil shall cause the diaphragm to engage either the permanent magnet or the valve plate.

11. The implantable diaphragm pump of claim 10 wherein said valve plate textured surface comprises a raised pattern wherein grooves of said raised pattern run in the direction in which fluid flows in said pump chamber.

* * * * *